(12) United States Patent
Demay et al.

(10) Patent No.: US 8,388,597 B2
(45) Date of Patent: *Mar. 5, 2013

(54) BAG SYSTEM WITH DEVICE FOR ASSOCIATING SAMPLING RECEPTACLES

(75) Inventors: Sylvie Demay, Halluin (FR); Francis Goudaliez, Faches-Thumesnil (FR); Thierry Verpoort, Mouxaux (FR)

(73) Assignee: Macopharma, Mouvaux (FR)

( * ) Notice: Subject to any disclaimer, the term of this patent is extended or adjusted under 35 U.S.C. 154(b) by 288 days.

This patent is subject to a terminal disclaimer.

(21) Appl. No.: 12/606,885

(22) Filed: Oct. 27, 2009

(65) Prior Publication Data
US 2010/0049089 A1 Feb. 25, 2010

Related U.S. Application Data

(63) Continuation of application No. 11/953,603, filed on Dec. 10, 2007, now Pat. No. 7,618,407, which is a continuation of application No. 10/782,077, filed on Feb. 19, 2004, now abandoned.

(30) Foreign Application Priority Data

Feb. 19, 2003 (FR) ..................................... 03 02034

(51) Int. Cl.
*A61B 19/00* (2006.01)
*A61B 5/155* (2006.01)
*A61M 5/32* (2006.01)

(52) U.S. Cl. ........ 604/409; 604/408; 604/410; 604/411; 604/412; 604/414

(58) Field of Classification Search .......... 604/408–410; 600/575, 577; 220/23.83
See application file for complete search history.

(56) References Cited

U.S. PATENT DOCUMENTS

| | | | |
|---|---|---|---|
| 3,501,131 A | 3/1970 | Grantham | 259/55 |
| 3,528,404 A | 9/1970 | Chan | 128/2 |
| 4,676,256 A | 6/1987 | Golden | 128/762 |
| 5,067,532 A | 11/1991 | Lang et al. | 141/329 |
| 5,125,920 A | 6/1992 | Ishida | 604/410 |
| 5,364,360 A | 11/1994 | Flumene et al. | 604/110 |
| 5,814,276 A | 9/1998 | Riggs | 42/65 |
| 5,871,699 A | 2/1999 | Ruggeri | 422/100 |
| 6,387,086 B2 | 5/2002 | Mathias et al. | 604/409 |
| 7,087,047 B2 | 8/2006 | Kraus et al. | 604/408 |
| 7,335,188 B2 | 2/2008 | Graf | 604/317 |
| 2001/0033233 A1 | 10/2001 | Jentsch et al. | 340/870.17 |
| 2004/0060859 A1 | 4/2004 | Seshimoto et al. | 210/416.1 |

FOREIGN PATENT DOCUMENTS

| | | |
|---|---|---|
| DE | 41 20 267 | 12/1992 |
| DE | 101 17 726 | 8/2002 |
| EP | 0 510 615 | 10/1992 |
| EP | 0 678 279 | 10/1995 |
| WO | 01/08546 | 2/2001 |

*Primary Examiner* — Susan Su
(74) *Attorney, Agent, or Firm* — Baker Botts L.L.P.

(57) ABSTRACT

The invention includes a bag system for collecting a biological fluid, in particular blood. The system includes a device for collecting the fluid which is in fluid communication with at least one fluid collection bag, and a device for sampling the fluid to be collected which includes at least one sampling receptacle. The sampling device includes a device for transferring the fluid from the bag system into the sampling receptacle or receptacles, in which the transfer device is provided with a device for associating the receptacle or receptacles. The transfer device may be arranged to allow the support of the receptacle or receptacles in a standby position, the guidance of the receptacle or receptacles to a transfer position and, after transfer, the dissociation of the receptacle or receptacles from the bag system.

14 Claims, 5 Drawing Sheets

BAG SYSTEM WITH DEVICE FOR ASSOCIATING SAMPLING RECEPTACLES

PRIORITY CLAIM

This application is a continuation of pending U.S. patent application Ser. No. 11/953,603 filed Dec. 10, 2007; which is a continuation of U.S. patent application Ser. No. 10/782,077, filed Feb. 19, 2004, which claims priority under 35 U.S.C. §119(d) to French Patent Application Serial No. 03/02034, filed Feb. 19, 2003, the contents of which are hereby incorporated in their entirety by reference.

FIELD OF THE INVENTION

The invention concerns a bag system for collecting a biological fluid in which sampling receptacles are associated.

BACKGROUND

Biological fluids such as whole blood must be collected from a donor in a collection bag. To accomplish this, one normally uses a the bag system including in closed circuit, a device for collecting the blood which is in fluid communication with at least one blood collection bag. In addition, the system includes a device for sampling the blood which is intended to receive some of the blood taken. The device normally includes at least one sampling receptacle.

The use of such a sampling device makes it possible to obtain, in each receptacle, a sample of blood intended to be analysed, in particular for carrying out serology, virology and a blood count.

In particular, the bag system may be used by collecting the first milliliters of blood in the sampling device, which has a certain number of advantages. Firstly, this reduces the risk of contamination resulting from the presence of bacteria or other foreign substances on the skin of the donor because the first milliliters of blood collected, which are more likely to be affected by this contamination, are sent into the sampling device rather than into the collection bag. Secondly, this makes it possible to take samples before the collection bag is completely filled and consequently does not waste time. Finally, during the collection, the loss of blood volume for the donor may be compensated for the addition of plasma, resulting in a lower haematocrit reading than if the sampling device were filled after the collection bag, and consequently the count would be incorrect.

One problem which is posed is that of the difficulty in handling known bag systems. This is because the user must position several receptacles in order to obtain the samples, which gives rise to a loss of time.

One aim of the invention is in particular to resolve this problem by proposing a bag system in which each sampling receptacle is stored at the device for transferring fluid from the bag system into it, the receptacle then being able to be guided by the operator into the transfer device for collecting a sample.

SUMMARY

The invention includes a bag system for collecting a biological fluid, in particular blood. The system includes a device for collecting the fluid which is in fluid communication with at least one fluid collection bag, and a device for sampling the fluid to be collected which includes at least one sampling receptacle. The sampling device includes a device for transferring the fluid from the bag system into the sampling receptacle or receptacles, in which the transfer device is provided with a device for associating the receptacle or receptacles. The association device is arranged to allow the support of the receptacle or receptacles in a standby position, the guidance of the receptacle or receptacles to a transfer position and, after transfer, the dissociation of the receptacle or receptacles from the bag system.

BRIEF DESCRIPTION OF THE DRAWINGS

Other objects and advantages of the invention will emerge during the following description given with reference to the accompanying drawings, in which.

DETAILED DESCRIPTION

Figure 1A:
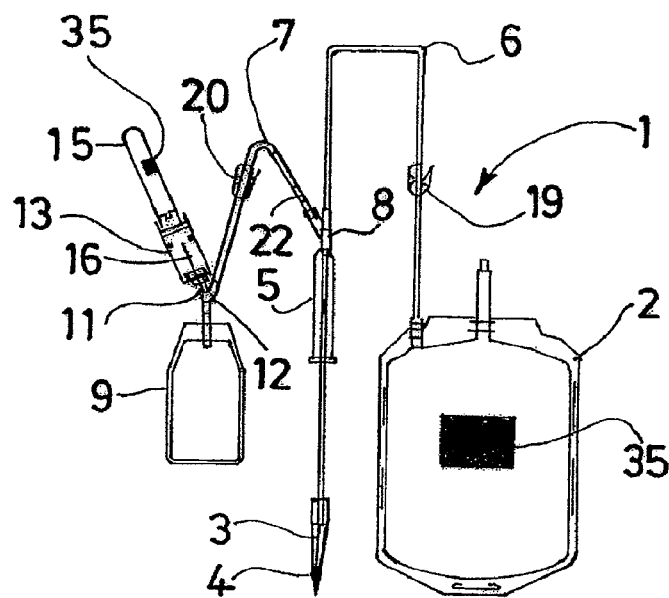
FIG. 1A depicts schematically a bag system for collecting blood which includes a sampling device according to a first embodiment.
Figure 1B:
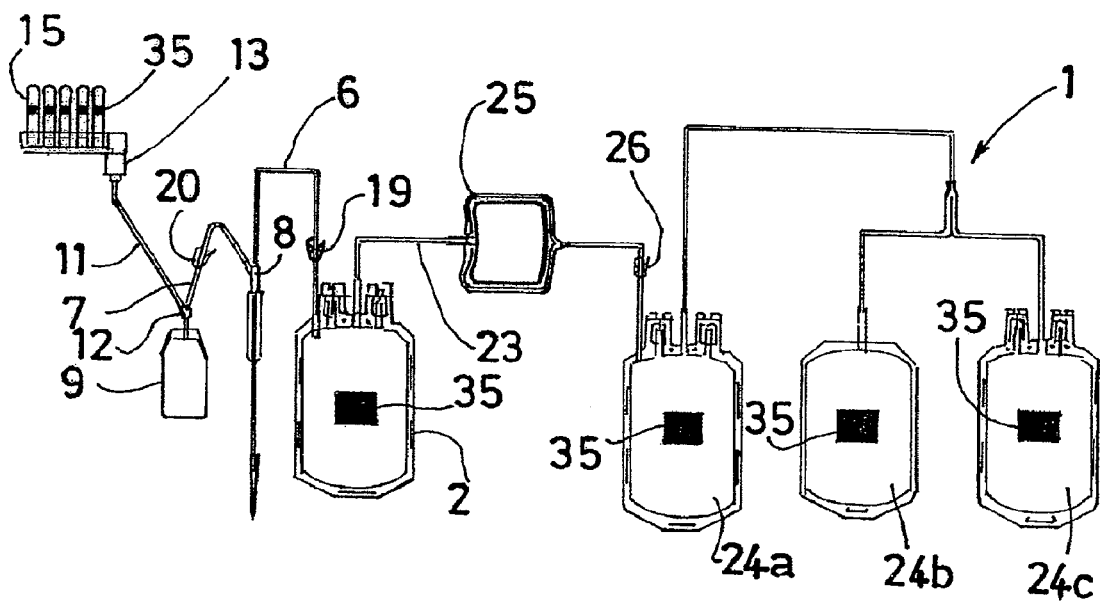
FIG. 1B depicts schematically a bag system for collecting blood and separating the blood components which includes a sampling device according to a second embodiment.

FIGS. 1A and 1B depict bag system 1 including a collection device for collecting fluid from a donor and at least one collection bag 2 intended to receive the fluid collected, in particular blood.

The collection device may consist in particular of needle 3 allowing access to the vein of the donor and cap 4 protecting needle 3. In addition, needle protector 5 may be placed slidably on first tube 6. First tube 6 places collection bag 2 in fluid communication with the collection device.

Bag system 1 also includes a sampling device, which is in fluid communication with collection bag 2 by way of first 6 and second 7 tubes connected at first connector 8 in the form of a three-way junction.

In the embodiments depicted, the sampling device includes sampling bag 9 which is connected to the downstream end of second tube 7. The terms downstream and upstream are defined with respect to the direction of flow of the blood, from the collection device to the bags and sampling device.

The sampling device also includes fluid transfer device 10 which is in fluid communication with collection bag 2 by way of first 6 and second 7 tubes, and possibly third tube 11 connected to second tube 7 at second connector 12 in the form of a three-way junction.

Figure 2:
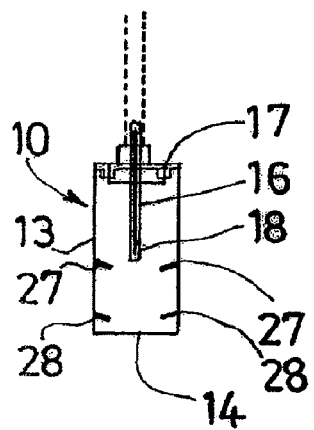
FIG. 2 depicts schematically the transfer device of the sampling device depicted in FIG. 1A.

As depicted in FIG. 2, transfer device 10 includes hollow guide 13, open at front part 14 to allow the insertion of sampling receptacle 15, and hollow needle 16 passing through rear part 17 of the guide, so that a downstream part of needle 16 extends inside guide 13 and an upstream part of needle 16 extends outside guide 13. The downstream segment of hollow needle 16 is enclosed in elastic sheath 18. The upstream segment of hollow needle 16 allows the connection of the transfer device with bag system 1. A fluid communication device or tube is then connected to the upstream segment.

First 19 and second 20 clamps may be situated respectively on first tube 6, downstream of connector 8, and on second tube 7. Clamps 19 and 20 make it possible to orient the flow of fluid collected, either to sampling bag 9, when first clamp 19 is closed while second clamp 20 is open, or to collection bag 2, when second clamp 20 is closed while first clamp 19 is open.

Sampling receptacle 15 is filled with the collected blood contained in sampling bag 9, when receptacle 15 is placed in the transfer position, namely when the downstream end of needle 16 is in fluid communication with the inside of receptacle 15, by perforation of closure element 21 of receptacle 15.

Circuit openers may be provided within bag system 1. In particular circuit opener 22 may be situated on second tube 7 close to first connector 8.

As depicted in FIG. 1B, in order to perform filtration and separation steps as well as the removal of the leukocytes from the various constituents of the blood, collection bag 2 may be in fluid communication, by way of fourth tube 23, with satellite bags 24a-c. Leukoreduction filter 25 may be situated between collection bag 2 and satellite bag 24a. Satellite bag 24a may be in fluid communication with one or more other satellite bags, for example satellite bag 24a may be in fluid communication with two other satellite bags 24b, c. Clamp 26 may be provided on fourth tube 23 between collection bag 2 and leukoreduction filter 25. According to one embodiment, satellite bags 24a-c may be provided with identification tag 35.

According to a first embodiment, transfer device 10 is provided with a device for associating sampling receptacle 15, as depicted in FIG. 2. The association device includes first 27 and second 28 sets of projections distributed longitudinally on the internal surface of guide 13, respectively close to needle 16 of the guide and close to front part 14 of guide 13. The projections are arranged so as to be deformable by sliding of receptacle 15 within guide 13 so as to allow a reversible association of receptacle 15 inside guide 13, and a sliding of receptacle 15 inside guide 13 between a standby position (FIG. 3A), at a distance from needle 16, and the transfer position (FIG. 3B).

Figure 3A:
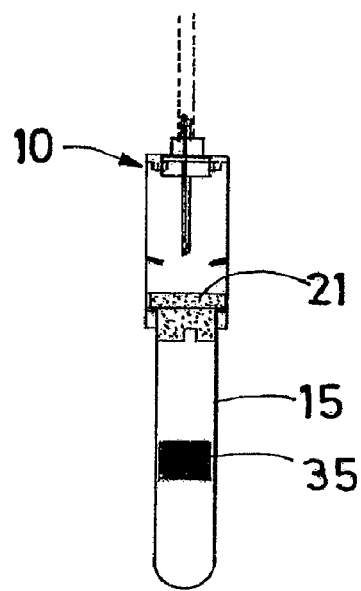
FIGS. 3A and 3B depict schematically the transfer device of FIG. 2 in which a sampling receptacle is disposed respectively in a position at a distance and in a transfer position.
Figure 3B:
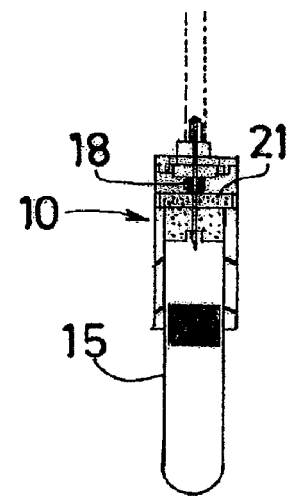

As depicted in FIGS. 2, 3A and 3B, the projections are flexible, in particular elastic, and are reversibly deformable from a forward inclined position to a rearward inclined position by contact of receptacle 15 when it slides inside guide 13 in the front to rear direction. When receptacle 15 is withdrawn from guide 13, the projections incline from rear to front so that the receptacle is not dissociated from its closure element 21. In the embodiment depicted, sampling receptacle 15 includes closure element 21 whose diameter is greater than that of the body of receptacle 15, it is during the passage of closure element 21 that the projections incline in one direction or the other.

Figure 3C:
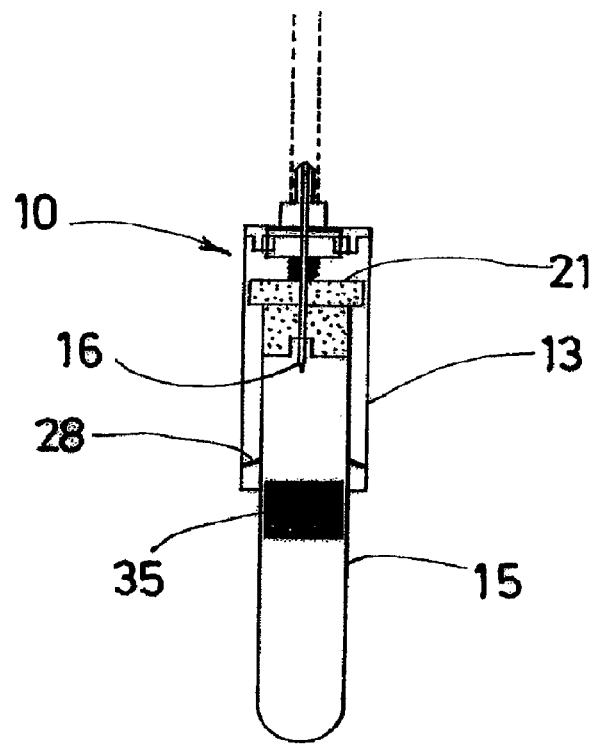
FIG. 3C is a representation similar to FIG. 3B showing a variant embodiment of the transfer device.

According to a variant, depicted in FIG. 3C, the projections of first set 27 situated close to needle 16 are breakable under the effect of the sliding of receptacle 15 placed in the transfer position. The perforation of closure element 21 is thus visible, and the user may check that the perforation has not taken place prior to the collecting of samples.

Figure 4:
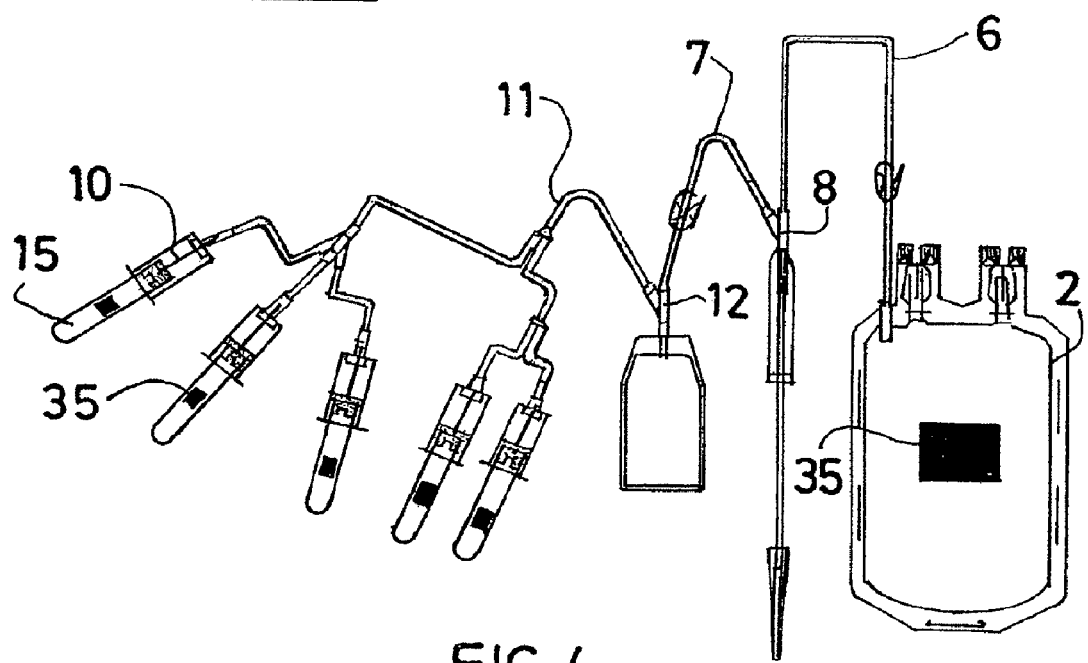
FIG. 4 depicts schematically a bag system for collecting blood which includes a sampling device provided with several transfer devices according to FIG. 2.
Figure 5A:
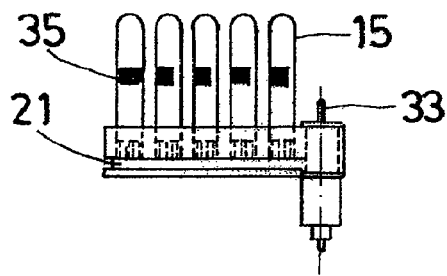
FIGS. 5A to 5E depict schematically the transfer device of the sampling device of FIG. 2, respectively front on, in perspective, in profile, in plan view and in transverse section, the sampling receptacles being in the standby position.
Figure 5B:
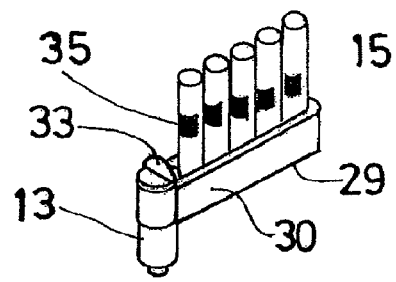
Figure 5C:
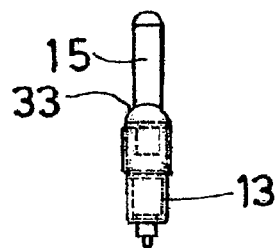
Figure 5D:
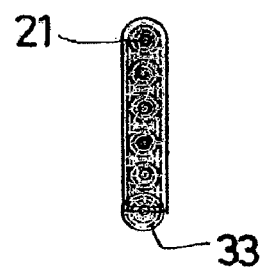
Figure 5E:
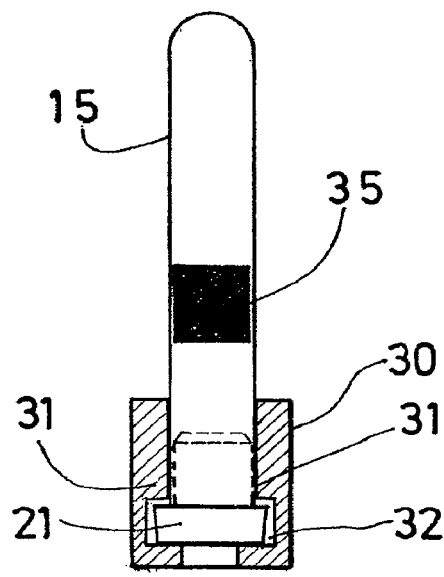

As depicted in FIG. 4, several transfer devices 10, in each of which one sampling receptacle 15 is associated in a dissociable fashion, may be connected to bag system 1 by way of second tube 7 or third tube 11, connected to second tube 7 by second connector 12. Associating several receptacles 15 in a dissociable fashion with several transfer devices 10 has advantages, firstly a saving in time for the person responsible for collecting the fluid because he or she does not need to place receptacle 15 in transfer device 10, and secondly a reduction in the risk of error in traceability of the donations, because this makes it possible to fix traceability labels prior to the collecting of samples, in particular at the time of manufacture.

According to a second embodiment, the association device is arranged to enable the supporting of several receptacles 15 at a distance from guide 13 in a standby position and their sequential guidance in guide 13, as depicted in FIGS. 1B and 5A to 5E.

The association device and the transfer device 10 may be associated by clipping on or welding, or may be moulded in one and the same piece.

The association device includes housing 29 associated with guide 13. Housing 29 is provided with skirt 30 in which closure element 21 of receptacles 15 is introduced to allow the longitudinal sliding of receptacles 15 in housing 29 towards guide 13. The internal wall of skirt 30 is provided with projection 31 intended, by interaction with closure elements 21, to prevent the transverse withdrawal of receptacles 15 from housing 29.

Skirt 30 includes an open end disposed opposite a scallop formed in the guide, and an opposite closed end. In the other axis, a first open end is disposed opposite the other end which is open so that the body of receptacle or receptacles 15 extends beyond housing 29.

At the time of manufacture, sampling receptacles 15 are introduced into guide 13 through its open front part 14 so that closure element 21 is situated level with groove 32 in housing 29 so that it may be slid therein.

Cap 33 is then placed on guide 13 making it possible to hold receptacles 15 in housing 29 until the samples are collected by the user of system 1.

The housing may be of variable size so as to contain from two to ten receptacles 15. The number of receptacles 15 used varies according to the legislation, in France foe example five receptacles 15 are used for carrying out normal analyses.

When samples are collected, the person responsible for collection removes cap 33 from guide 13, makes receptacles 15 slide as far as guide 13, and then introduces them so that, by perforation of closure element 21 of receptacle 15, the downstream end of needle 16 is in fluid communication with the inside of receptacle 15. After receptacle 15 has been filled, the user withdraws it from guide 13. In one example embodiment, cap 33 may be provided with a tamper-evident element, such as a tongue which is broken on first opening, so as to be able to identity the first handling of cap 33.

Figure 6A:
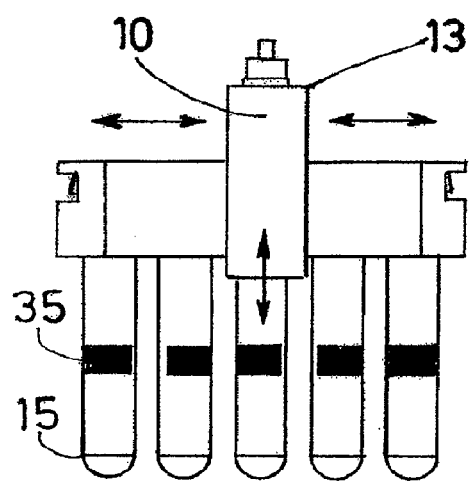
FIGS. 6A and 6B depict schematically the transfer device of FIG. 5 according to a variant embodiment, respectively front on and in profile, the receptacles being in the standby position.
Figure 6B:
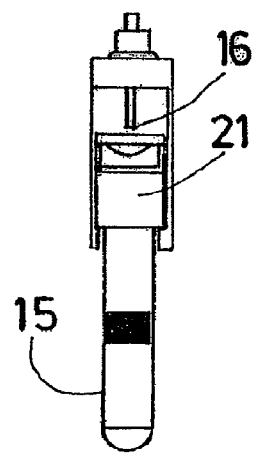
Figure 6C:
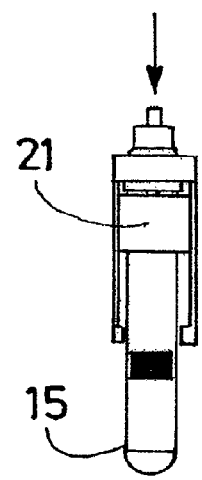
FIG. 6C is a view similar to FIG. 6B in which a receptacle is in the transfer position.

According to a variant, depicted in FIGS. 6A to 6C, transfer device 10 may slide on the association device, so that it may be placed level with each receptacle 15. When transfer device 10 is placed level with receptacle 15, the user may then move transfer device 10 transversely so that closure element 21 is perforated by needle 16. So that transfer device 10 may slide on the association device, two opposite scallops are then formed in guide 13.

As depicted in FIG. 1B, transfer device 10 associating several sampling receptacles 15 may be connected to bag system 1 by way of second tube 7 and possibly third tube 11.

With known bag systems for collecting blood, the person responsible for collection must identify, by way of a mark, collection bag 2 and sample receptacle or receptacles 15 corresponding to one and the same donation.

According to the invention, the possibility of error in traceability of these donations is considerably reduced because sampling receptacle or receptacles 15 and collection bag 2 are associated at the time of manufacture in a dissociable fashion. In addition, upon manufacture, collection bag 2 and sampling receptacle or receptacles 15, as well as satellite bags 24*a-c*, are each provided with identification tag 35, for example by way of a self-adhesive label with bar codes, which includes information making it possible, after dissociation of the receptacle from bag system 1, to unequivocally establish that sampling receptacle 15 and collection bag 2, as well as any satellite bags 24*a-c*, come from the same bag system 1.

The invention claimed is:

1. A bag system for collecting a biological fluid comprising:
   a collection device;
   a fluid collection bag in fluid communication with the collection device; and
   a sampling device in fluid communication with the collection device, the sampling device including:
   at least one sampling receptacle;
   a transfer device having an associating device having a hollow guide open at a front part to allow introduction of the at least one sampling receptacle and one or more flexible projections on an internal face of the hollow guide,
   wherein the one or more flexible projections are arranged so as to be deformable by sliding the at least one sampling receptacle inside the hollow guide, and wherein at least one of the one or more flexible projections is reversibly deformable from a position inclined towards the front part of the hollow guide to a position inclined towards a rear part of the hollow guide by contact of the at least one sampling receptacle while sliding inside the hollow guide in a front to rear direction, and from a position inclined towards the rear of the hollow guide to a position inclined toward the front of the hollow guide by contact of the at least one sampling receptacle while sliding inside the hollow guide in a rear to front direction, and
   wherein the associating device is operable to support the at least one sampling receptacle in a standby position, guide the at least one sampling receptacle to a transfer position, and allow dissociation of the at least one sampling receptacle from the bag system.

2. The system of claim 1, wherein the biological fluid comprises blood.

3. The system of claim 1, further comprising:
   a first tube to establish fluid communication between the collection device and the fluid collection bag; and
   a second tube to establish fluid communication between the collection device and the sampling device.

4. The system of claim 3, wherein the sampling device further comprises a sampling bag connected to the downstream end of the second tube.

5. The system of claim 1, wherein the receptacle has a body having a first diameter and further comprises a closure element having a second diameter greater than the first diameter.

6. The system of claim 1, wherein the transfer device further comprises:
   a hollow needle in fluid communication with the bag system,
   wherein the hollow needle passes through the rear part of the hollow guide so that a downstream part of the needle extends inside the hollow guide and an upstream part of the needle extends outside the hollow guide, and wherein the hollow needle is operable to perforate a closure element of the sampling receptacle, so as to place the downstream part of the needle inside the sampling receptacle.

7. The system of claim 6,
   wherein the one or more flexible projections are arranged so as to permit sliding of the receptacle inside the guide between the standby position at a distance from the needle and the transfer position.

8. The system of claim 6, further comprising a set of projections located near the hollow needle, wherein said set of projections are breakable under the deformation.

9. The system of claim 1, further comprising a first tube to establish fluid communication between the collection device and the fluid collection bag;
   a second tube to establish fluid communication between the collection device and the sampling device; and
   a plurality of transfer devices, each having a sampling receptacle associated in a dissociable fashion and each in fluid communication with the bag system through the second tube or a third tube.

10. The system of claim 1, wherein the at least one sampling receptacle comprises a plurality of sampling receptacles, the system further comprising a first tube to establish fluid communication between the collection device and the fluid collection bag;
    a second tube to establish fluid communication between the collection device and the sampling device; and
    the transfer device having the plurality of sampling receptacles associated therewith and the transfer device is in fluid communication with the bag system through the second tube or a third tube.

11. The system of claim 1, further comprising at least two identification tags, one disposed on the collection bag and the other disposed on the at least one sampling receptacle, wherein the tags allows the establishment, after their dissociation, that both the collection bag and the at least one sampling receptacle originated from the same bag system.

12. The system of claim 11, further comprising a tube in fluid communication with the collection bag and at least one satellite bag, wherein the satellite bag is also provided with an identification tag.

13. A method of collecting a biological fluid comprising:
    placing a collection device in a donor;
    collecting the fluid in a sampling device having at least one sampling receptacle and a transfer device having an associating device having a hollow guide open at a front part to allow introduction of the at least one sampling receptacle and one or more flexible projections on an internal face of the transfer device, wherein the flexible projections are arranged so as to be deformable by sliding the at least one sampling receptacle inside the hollow guide, and wherein at least one of the one or more flexible projections is reversibly deformable from a position inclined towards the front part of the hollow guide to a position inclined towards a rear part of the hollow guide by contact of the at least one sampling receptacle while sliding inside the hollow guide in a front to rear direction, and from a position inclined towards the rear of the hollow guide to a position inclined toward the front of the hollow guide by contact of the at least one sampling receptacle while sliding inside the hollow guide in a rear to front direction;

placing a first sampling receptacle of the at least one sampling receptacle in a standby position in the association device of the transfer device;

moving the first sampling receptacle to a transfer position in the transfer device to allow flow of the biological fluid into the first sampling receptacle;

dissociating the first sampling receptacle from the association device.

14. The method of claim 13, wherein the at least one sampling receptacle comprises a plurality of sampling receptacles, the method further comprising:

moving a second sampling receptacle of the plurality of sampling receptacles in the association device from the standby position to the transfer position; and dissociating the second sampling receptacle from the association device.

* * * * *